United States Patent
Jahnke et al.

[11] Patent Number: 5,928,433
[45] Date of Patent: Jul. 27, 1999

[54] SURFACTANT-ASSISTED SOIL REMEDIATION

[75] Inventors: Richard W. Jahnke, Mentor; Bryan A. Grisso, Wickliffe, both of Ohio

[73] Assignee: The Lubrizol Corporation, Wickliffe, Ohio

[21] Appl. No.: 09/090,738

[22] Filed: Jun. 4, 1998

Related U.S. Application Data

[60] Provisional application No. 60/062,855, Oct. 14, 1997.

[51] Int. Cl.$^6$ .............................. C03C 23/00; A62D 3/00
[52] U.S. Cl. ................................ 134/2; 588/249
[58] Field of Search .................. 134/2; 523/134; 524/442, 368

[56] References Cited

U.S. PATENT DOCUMENTS

| | | | |
|---|---|---|---|
| 4,632,742 | 12/1986 | Tundo | 204/158.21 |
| 4,664,834 | 5/1987 | Forsberg | 252/77 |
| 4,997,313 | 3/1991 | Givson et al. | 405/128 |
| 5,008,019 | 4/1991 | Trost | 210/747 |
| 5,240,570 | 8/1993 | Chang et al. | 204/130 |
| 5,376,182 | 12/1994 | Everett et al. | 134/25.1 |
| 5,425,881 | 6/1995 | Szejtli et al. | 210/747 |
| 5,427,688 | 6/1995 | Sivavec | 210/639 |
| 5,615,975 | 4/1997 | Wang et al. | 405/128 |
| 5,618,727 | 4/1997 | Lajoie et al. | 435/262.5 |
| 5,671,762 | 9/1997 | Hancock et al. | 134/65 |
| 5,725,470 | 3/1998 | Lazarowitz et al. | 588/249 |

OTHER PUBLICATIONS

Shiau et al., "Surfactant Selection for Optimizing Surfactant–Enhanced Subsurface Remediation," ACS Symposium Series 594, Surfactant–Enhanced Subsurface Remediation, 1995, pp. 65–79.

*Primary Examiner*—Jill Warden
*Assistant Examiner*—Yolanda E. Wilkins
*Attorney, Agent, or Firm*—David M. Shold

[57] ABSTRACT

A surfactant which is the reaction product of a hydrocarbyl-substituted succinic anhydride or a reactive equivalent thereof with at least one water-dispersible amine-terminated poly(oxyalkylene), is effective for use in soil remediation.

27 Claims, No Drawings

SURFACTANT-ASSISTED SOIL REMEDIATION

This application claims priority from United States Provisional Application 60/062,855, filed Oct. 14, 1997.

BACKGROUND OF THE INVENTION

The present invention relates to a method for removing organic contamination from soils, involving the use of a certain surfactant-containing composition to facilitate the removal.

Removal of organic contaminants or pollutants from soil is of great concern. Conventional pump-and-treat remediation, however, has met with limited success, often due to the presence of residual saturated domains of contaminant or strong sorption of the contaminant onto soil components.

Surfactants have been employed in an attempt to enhance subsurface remediation. A review of such techniques has been published by Sabatini et al., "Emerging Technologies in Surfactant-Enhanced Subsurface Remediation," ACS Symposium Series 594, Surfactant-Enhanced Subsurface Remediation, 1995, pages 1–6.

Details of surfactant selection for such use, especially for removal of chlorinated organic contaminants, has been published by Shiau et al., "Surfactant Selection for Optimizing Surfactant-Enhanced Subsurface Remediation," pages 65–79 of the aforementioned ACS Symposium Series 594. This reference discloses that surfactants can improve subsurface remediation by solubilization (increasing the aqueous concentration of the contaminant by partitioning into surfactant micelles) or microemulsification (formation of a middle phase microemulsion with concomitant ultra-low interfacial tensions.) The high performance surfactants which were utilized are alkyl diphenyloxide disulfonates from the DOWFAX™ series, ranging from 10 to sixteen carbons in the alkyl group. Surfactant type (structure) is disclosed to be critical to achieving microemulsification systems, unlike solubilization systems where enhancement is relatively independent of surfactant type. Advantages of the DOW-FAX™ surfactants include their resistance to precipitation in the presence of calcium ion and minimal susceptibility to sorption losses. Reference to this article can be made for detailed information relative to the theory and practice of various types of micellar and middle-phase systems involving surfactants, useful concentrations, their preparations, and their relative advantages.

A variety of surfactants are known for industrial and other applications. U.S. Pat. No. 4,664,834, Forsberg, May 12, 1987, discloses a water-dispersible reaction product of (A) at least one compound represented by the formula

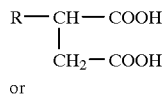

or

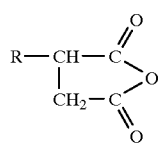

herein R is a hydrocarbyl group of from about 8 to about 40 carbon atoms, with (B) at least one water-dispersible amine terminated poly(oxyalkylene). Aqueous concentrates and water-based functional fluid comprising these compositions are also disclosed. These reaction products are useful as shear-stable thickeners for such functional fluids.

SUMMARY OF THE INVENTION

The present invention provides a method for remediating soil which is contaminated by one or more organic chemicals, comprising:

(a) contacting the contaminated soil with an aqueous composition comprising a surfactant represented by the structure

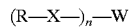

where;
each R is independently a hydrocarbyl group containing at least 8 carbon atoms,
n is at least 1,
W is a group containing at least 6 carbon atoms and at least one ether linkage for every 6 carbon atoms thereof, and
each X is selected from the group consisting of

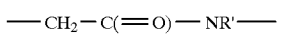

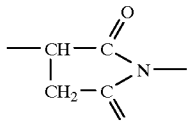

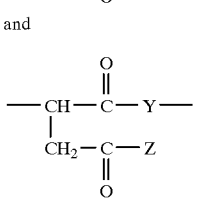

and

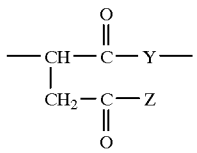

where:
each Y is independently —O— or —NR'—,
each Z is independently OM or NR'$_2$,
each R' is independently hydrogen or a $C_1$ to $C_{18}$ alkyl group,
M is hydrogen, a monovalent metal or one valence of a polyvalent metal, a quaternary ammonium ion, a $C_1$ to $C_{18}$ alkyl group, or —(CH$_2$CHR"O)$_a$—H, where R" is hydrogen or a methyl group and a is 1 to 40;
wherein the group X is connected to the group W through the group Y or —NR'—;
whereby at least a portion of said hydrophobic organic chemicals become associated with said aqueous composition.

Thereafter the aqueous composition and organic chemicals associated therewith can be removed from the soil, or they can be decontaminated by a biological process.

The present invention further provides surfactants suitable for such use, including a composition represented by the structure

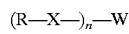

where:
n is 1;
R is independently a hydrocarbyl group containing at least 8 carbon atoms,
W is a group containing at least 6 carbon atoms and at least one ether linkage for every 6 carbon atoms thereof, having no unreacted amino groups
and where X is selected from the group consisting of

—CH$_2$—C(═O)—NR'—

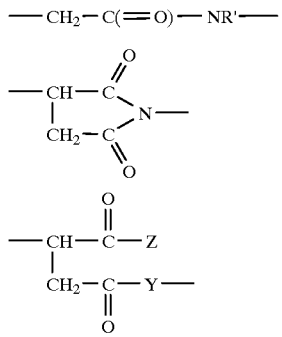

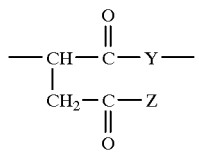

where:
Y is —O— or —NR'—,
Z is OM or NR'$_2$,
each R' is independently hydrogen or a $C_1$ to $C_{18}$ alkyl group,
M is hydrogen, a monovalent metal or one valence of a polyvalent metal, a quaternary ammonium ion, a Cl to $C_{18}$ alkyl group, or —(CH$_2$CHR"O)$_a$—H, wherein a is 1 to 40 and R" is hydrogen or a methyl group;
wherein the group X is connected to the group W through the group Y or —NR'—.

DETAILED DESCRIPTION OF THE INVENTION

In the process of the present invention, the term "soil" is used in a generic sense to refer to the various materials which can be encountered in the earth and which can be the subject of contamination. Soil, therefore, includes rocks, sand, gravel, clays, silt, humus, loess, and other such components, alone or in combination, and including varying amounts of water which may be found in the presence of such components, as is found in the ground. The particular composition of soil varies from location to location in a way which is widely recognized and is well known to those skilled in the art. The particular type of soil for which the present invention is suitable is not particularly limited. For testing and evaluation purposes, a standard soil known as "Canadian River Alluvium," consisting of 72% sand, 27% silt and clay (on a dry basis), and an organic carbon content of 0.07%, is sometimes employed.

Soil can be contaminated by a variety of exogenous organic materials. The contaminants can be associated with the solid components of the soil or the water component of the soil (i.e., groundwater) or both. These contaminants are often characterized by a greater or lesser degree of hydrophobicity, water insolubility, and sometimes a tendency sorb to various soil components. These properties make remediation of the soil more difficult. Common contaminants include crude oils, that is, mineral oils, petroleum, solvent or acid treated mineral oils, and oils derived from coal or shale. Synthetic oils can also be contaminants: these include hydrocarbon oils, halo-substituted hydrocarbon oils, alkylene oxide polymers, esters of dicarboxylic acids and polyols, esters of phosphorus-containing acids, polymeric tetrahydrofurans and silicon-based oils. Also included are crude oil fractions and refined hydrocarbons such as gasolines, kerosene, diesel fuel, and fuel oil. Also included are commercial oil-containing compositions, such as motor oils and other lubricants, transmission fluids, and hydraulic fluids.

Other common organic contaminants include halogenated hydrocarbons, commonly chlorinated hydrocarbons, which are sometimes used as solvents or synthetic lubricants. Examples of chlorinated organic contaminants include solvents such as tetrachloroethylene, trichloroethylene, and trans-1,2-dichlorethylene. Other contaminants can include aromatic substances such as benzene, toluene, and naphthalene, as well as various aliphatic hydrocarbons.

The foregoing contaminants may be associated with the solid soil particles, with the water component of the soil, or in any combination thereof.

An important component of the present invention is the surfactant. The surfactant is represented by the structure (R—X—)$_n$—W. The expression "represented by the structure" is meant to include obvious variants and equivalent of a given structure, including isomers, tautomers, and the like. In the structure above, each R is independently a hydrocarbyl group containing at least 8 carbon atoms, and preferably up to 40 carbon atoms. Preferably each R is an alkyl group of 12 to 32, or more preferably 16 to 18 carbon atoms. The R groups are intended to provide a measure of hydrophobic character to the surfactant molecule.

In the above structure, each X is a carbonyl-containing linking group, represented by one or more of the structures

—CH$_2$—C(═O)—NR'—

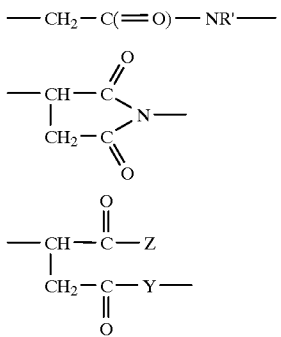

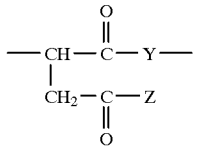

where:
each Y is independently —O— or —NR'—,
each Z is independently OM or NR'$_2$,
each R' is independently hydrogen or a $C_1$ to $C_{18}$ alkyl group,
M is hydrogen, a monovalent metal or one valence of a polyvalent metal, a quaternary ammonium ion, a $C_1$ to $C_{18}$ alkyl group, or —(CH$_2$CHR"O)$_a$—H, R" is hydrogen or methyl, and a is 1 to 40.

In the structures shown, it is recognized that normally the group X is connected to the group W through the group Y or —NR'—, as the case may be. It will be recognized that these are ester, amide, or imide structures.

Preferably X is a structure containing two carboxylic moieties, that is, a succinic acid-type structure. Preferably Y is NR', more preferably NH. Preferably Z is OM and preferably M is a monovalent metal, preferably an alkali metal, more preferably sodium.

In a preferred embodiment, each X group is represented by the structure

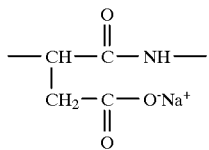

This represents an alkyl-substituted succinamide structure, which is at least in part in the form of the sodium salt. Alkyl-substituted succinamides are well known materials which have been set forth, i.a., in U.S. Pat. No. 4,664,834, described above. They can be prepared by, first, reacting an olefin (providing the R group) with the desired unsaturated carboxylic acid such as fumaric acid or a derivative of such an acid such as maleic anhydride at a temperature in the range of, for example, 160° C. to 240° C., preferably 185° C. to 210° C. Generally these reactions are conducted at an atmospheric pressure, although elevated pressures can also be used. Free radical inhibitors (e.g., t-butyl catechol) can be used to reduce or prevent the formation of polymeric by-products. Further details can be found in Benn et al., "The Ene Reaction of Maleic Anhydride with Alkenes," J. C. S Perkin II (1977) pp 535–7. After the initial reaction with of the olefin with the unsaturated acid or equivalent, the alkylated product is further reacted with a suitably terminated W group to form an ester or, preferably, an amide.

In the structure (R—X)$_n$W, n is at least 1 but is normally 2 or more, preferably 2. Corresponding to the value of n, W is a mono- or polyvalent group.

The W group of the surfactant is believed to provide a measure of hydrophilic character to the molecule. The group W is preferably a polyvalent group, normally a divalent group, so that n in the above formula is normally 2. The W group contains at least 6 carbon atoms, and preferably 20 to 300 carbon atoms, more preferably 40 to 200 carbon atoms, and moreover contains at least one ether linkage for every 6 carbon atoms, and preferably for every 4 carbon atoms. The group W preferably comprises polymerized ethylene oxide monomers and propylene oxide monomers. In one embodiment, W is represented by the structure

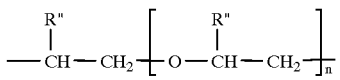

where n is at least 2 and each R" is independently hydrogen or methyl. That is, monomer units derived from ethylene, propylene, or mixtures thereof can be used. In a preferred embodiment, W is represented by the structure

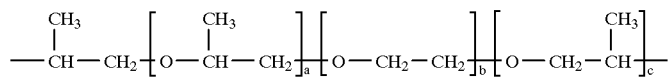

where a and c are integers which together equal 2 to 20 (preferably 3 to 20) and b is an integer in the range of 5 to 70 (preferably 20 to 70).

In a preferred embodiment, the W group is terminated by amine functionality, to provide the amides characteristic of the preferred X groups, above. W then represents the central moiety of an amine-terminated poly(oxyalkylene). Preferred examples of such amine terminated materials can be described as alpha, omega diaminopropyleneoxide-capped poly(oxyethylene)s, when n is 2. If n is 1, W would be a corresponding monoamino polyoxyalkylene moiety, the non-nitrogen terminated end of which would normally be terminated with a nonreactive group such as an alkyl (e.g., methyl, ethyl, propyl) group. It is also possible that additional amino groups are present within the structure of W. These materials are available from the Huntsman corporation. A material referred to as Huntsman™ XTJ-502 (also referred to as Jeffamine™ ED-2003), which is an alpha, omega diamino poly(oxyalkylene) is particularly preferred.

A preferred surfactant for use in the present invention is a sodium salt represented by the structure

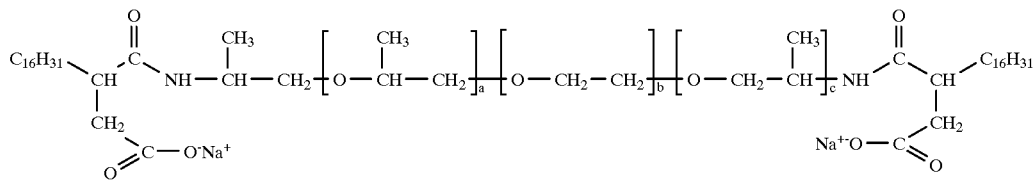

and positional isomers thereof; that is, the C$_{16}$H$_{31}$ groups may be attached to either of the two carbon atoms shown. In this preferred case, a and c are integers which together equal 4 to 6, c is a positive integer, and b is an integer in the range of 30 to 50, and more preferably about 40. Such materials have good resistance to Ca ion (water hardness) and low sorption onto soil, as well as an excellent ability to dissolve or emulsify contaminants.

In an alternative embodiment, W can be a monovalent moiety containing at least 20 carbon atoms and at least one ether linkage for every 6 carbon atoms thereof, having no unreacted amino groups. One species of W, in this case, is represented by the structure

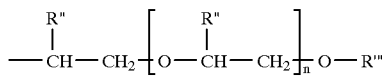

A preferred species of W is that represented by the structure

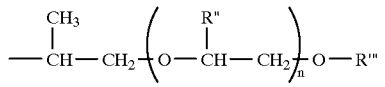

where, in each of the preceeding structures, each R" is independently hydrogen or methyl, R'" is hydrogen or a $C_1$ to $C_4$ alkyl group, and n is at least 5. Preferably the ratio of the hydrogen to methyl groups of R" is 3:1 to 8:1, preferably 5:1 to 8:1, (e.g, about 19:3), R'" is a methyl group, and n is 5 to 42, preferably 8 to 42, or 15 to 42, or more preferably 20 to 24 (e.g., about 22).

Alternatively expressed, the preferred surfactant can be described as a reaction product of a hydrocarbyl-substituted succinic anhydride or a reactive equivalent thereof with at least one water-dispersible amine-terminated poly (oxyalkylene). The components are typically prepared by reacting the hydrocarbyl-substituted succinic anhydride with the amine-terminated poly(oxyalkylene) at temperatures of 60° C. to about 160° C., preferably 120° C. to 160° C. The ratio of the anhydride to the diamine is typically 0.1:1 to 8:1, preferably 1:1 to 4:1, and more preferably about 2:1. The resulting material is normally an amid/acid, that is, a half amide. The product can be neutralized with a basic material using methods well known in the art, to form a salt, preferably a sodium salt. Such materials and their preparation are described in greater detail in U.S. Pat. No. 4,664,834.

The above-described surfactant is used in water, generally at a concentration of 0.005 to 5 weight percent, preferably 0.25 to 3 percent and more preferably 2 to 3 percent (based on active chemical, exclusive of diluent water). The amounts can be adjusted, as needed, to optimize performance for a particular combination of soil and contaminant. For in situ remediation, concentrations of 1 to 3 weight percent are sometimes preferred; for ex situ remediation (where soil is removed from the ground and treated), concentrations of 0.01 to 0.5 weight percent are sometimes preferred. The surfactant can be dissolved or otherwise dispersed in the water; preferably the surfactant is dissolved.

If desired, one or more additional surfactants, preferably in amounts within the ranges set forth above, can be used along with the above-described materials. Common surfactants can be characterized as non-ionic, anionic, cationic, or amphoteric. Non-ionic surfactants include nonylphenol (POE5), octylphenol(POE5), lauryl alcohol(POE5), octadecyl alcohol(POE5), sorbitan monooleate, sorbitan monooleate(POE5), glycerol monooleate, lauryl alcohol polyglycoside, oleicdiethanolamide, oleylhydroxymethyl imidazoline, oleylamine(POE5), oleyl dimethylamine oxide, poly(ethylene oxide [m.w. 400]) dioleate, and poly(ethylene oxide) 14 oleate.

Anionic surfactants include sodium laurate, sodium xylene sulfonate, sodium dodecylbenzene sulfonate, sodium monomethylnaphthalene sulfonate, sodium dimethylnaphthalene sulfonate, dioctyl sodium sulfosuccinate, sodium hexadecyl sulfonate, dodecyldiphenyloxide disulfonate (disodium salt), hexadecyldiphenyloxide disulfonate (disodium salt), sodium decyl sulfate, sodium lauryl(POE2) sulfate, nonylphenol(POE2) sulfate (sodium salt), sodium N-methyl-N-oleoyl taurate, sodium di-2-ethylhexyl phosphate, sodium cocyl isethionate, and sodium lauryl (POE13) acetate.

Cationic surfactants include benzyl trimethylammonium bromide and cetyl pyridinium chloride. Amphoteric surfactants include lecithin and lauryldimethylhydroxypropylsulfobetaine.

In the foregoing materials, the expression "POEn" indicates an ethylene oxide oligomer containing n repeat units, attached by an ether linkage through an alcoholic or phenolic oxygen atom of the remainder of the molecule.

The surfactant-water combination is used to contact the contaminated soil and to remove organic contaminants therefrom by mechanical techniques which are known to those skilled in the art. Using a process based on the conventional "pump and treat" procedure, the aqueous composition can be injected into the ground at or near a site of contamination, and a water composition, comprising the surfactant and a portion of the contaminants, can be pumped out from the ground in such a way that the water/surfactant composition has traversed at least a portion of the contaminated soil. The aqueous composition thereby recovered can be treated for waste processing and management. Such treatment can consist of separation of the contaminant from the water and surfactant by known means such as air stripping, foam fractionation, distillation, coagulation, solidification, filtration, or other such techniques, and subsequent disposal of the contaminant, for example, by combustion. It is also possible to recover some or all of the surfactant for reuse, if desired.

Alternatively, a portion of contaminated soil can be removed from the ground and treated with a suitable aqueous solution of surfactant in an appropriate apparatus. The soil can be contacted with the surfactant solution by stirring or slurrying in a batch-type operation, or by passing the solution through the soil in a continuous fashion. The aqueous solution, containing a portion of the organic contaminant, can be separated from the soil by known methods such as filtration, decantation, or centrifugation. Remediation by removal of the soil and treatment in this manner is particularly suitable for small and localized areas of contamination or for spot testing and evaluation purposes.

In yet another approach, the surfactants of the present invention can be used in surfactant-assisted bioremediation processes, that is, a process in which the decontamination is effected by a surfactant-assisted biological process. In such processes, it is speculated that the surfactant may serves to "loosen" the contaminant from the soil particles and make it more readily available for decontamination. The contamination itself is effected, optionally in situ, by biological processes resulting from, for instance, the action of bacteria or other organisms, whether organisms naturally occurring (naturally present in the soil) or selected or designed for the purpose of decontamination. In this embodiment, physical removal of the aqueous compositions and organic chemicals associated therewith from the soil may not be necessary.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

It is known that some of the materials described above may interact in the final formulation, so that the components of the final formulation may be different from those that are initially added. For instance, metal ions (of, e.g., a detergent) can migrate to other acidic sites of other molecules. The products formed thereby, including the products formed upon employing the composition of the present invention in its intended use, may not susceptible of easy description. Nevertheless, all such modifications and reaction products are included within the scope of the present invention; the present invention encompasses the composition prepared by admixing the components described above.

EXAMPLES

Certain of the tests reported below are performed using a surfactant represented by the structure

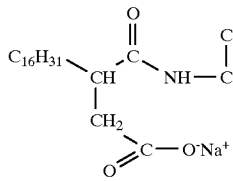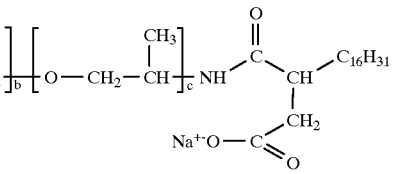

where a and c are integers which together equal 4 to 6 and b is an integer in the range of 30 to 50. This surfactant is hereinafter referred to as Surfactant A.

Example 1

A. 2960 parts of C16 alpha olefin and 100 parts of Amberlyst™ 15 (a product of Rohm & Haas Company identified as a cation exchange resin) are added to a five-liter flask equipped with a nitrogen sparge at 57 L/hr (2.0 std. ft³/hr), stirrer, thermowell, and water trap positioned below a condenser. The mixture is heated to 120° C. for 1.5 hours with the stirrer operating at 350 rpm. The filtrate is isolated.

B. 367.5 parts of maleic anhydride are added to a two-liter flask equipped with stirrer, thermowell, reflux condenser, and gas inlet tube. The maleic anhydride is melted and 765 parts of the product from part A are added. The mixture is heated to 180 to 200° C. for 9.75 hours. The mixture is stripped under a vacuum of 30 mm Hg at 182° C., then cooled to 115° C. The mixture is then stripped under a vacuum of 0.7 mm Hg at 145° C., then cooled to 50° C. The mixture is filtered with diatomaceous earth, and the filtrate retained.

C. 100 parts of Jeffamine™ ED-4000 (a diamine having an average molecular weight of about 4000 and being a primary amine terminated propylene oxide capped polyoxyethylene) and 16.3 parts of the product from part B of this example are mixed together, heated at a temperature of 130° C. for three hours, and then cooled to room temperature. The mixture is diluted with 116.3 parts water in one portion. At 45° C., the mixture is neutralized with 4.0 parts of 50% aqueous sodium hydroxide and filtered to provide the desired product (including diluent water).

Example 2

A glass lined, jacketed reactor vessel, equipped with an agitator, condenser, and nitrogen flow, is heated to 85° C. To this vessel is charged 100 parts by weight Jeffamine™ ED-2003 (a diamine with terminal amine groups, internal ether linkages, and a molecular weight of about 2,000), with stirring. To the vessel is added 30.9 parts hexadecenyl succinic anhydride over 30 minutes, during which time the reaction temperature increases to about 93° C. Thereafter the mixture is heated to about 100° C. and maintained at temperature for 3 hours.

The reaction mixture is cooled to 45° C. and 131 parts water is added as diluent, as well as 0.8 parts silicone antifoam agent. The mixture is maintained, with stirring, at 40° C. for 1 hour.

To the mixture is added 9.0 parts of 50% aqueous sodium hydroxide solution over 15 minutes, during which time the temperature is maintained at below 50° C.; stirring is continued to effect complete reaction.

The resulting mixture is filtered through a filter aid to provide 269 parts of product ("Surfactant A") including diluent water.

Example 3

Example 2 is substantially repeated except that the Jeffamine™ ED-2003 amine is replaced by 300 parts by weight of a similar material of about 6000 molecular weight. The amount of diluent water added is adjusted accordingly to provide a 50% by weight concentration of chemical in the resulting mixture.

Example 4

Example 3 is substantially repeated except that the amine is replaced by 60 parts by weight of a similar material of about 600 molecular weight.

Example 5

Dodecenyl-succinic anhydride is prepared by a method similar to that of Example 1 A and B, except that a C12 alkyl group is provided.

To a 2 L, 4-necked flask equipped with a stirrer, thermowell, water condenser, and addition funnel with nitrogen inlet, is charged 500 g of Jeffamine™ ED-2003. The contents of the flask are heated with stirring to 50° C. under a nitrogen flow of 14L/hr (0.5 std. ft$^3$/hr), and the dodecenyl succinic anhydride is added dropwise from the addition funnel over 30 minutes. During the course of addition the temperature of the mixture increases to 87° C. The mixture is further heated to 100° C. with stirring. After 1 hour at 100° C., infrared analysis of the mixture indicates substantially complete reaction. After a total of 4 hours at 100° C., the composition is allowed to cool to 44° C. To the composition, 633 g water is added in one portion, causing the mixture to become slightly foamy. At 44° C., 40 g of 50% aqueous sodium hydroxide solution is added dropwise over 20 minutes. During this addition, the temperature of the composition increases to 49° C. After maintaining the composition at temperature for 40 minutes, it is poured into jars without filtration. The product is a dark brown foamy liquid.

Example 6

To a 2 L, 4-necked flask equipped with a stirrer, thermowell, water condenser, and addition funnel with nitrogen inlet is charged 575 g of Jeffamine™ M-1000 (a monoamine having an average molecular weight of about 1150 and being a primary amine-terminated propylene oxide capped poly(oxyethylene)). The contents of the flask are heated with stirring to 50° C. under a nitrogen flow of 14 L/hr (0.5 std. ft$^3$/hr), and 161 g of the product from Example 1, part B are added dropwise from the addition funnel over 20 minutes. During the addition the temperature of the mixture increases to 62° C. The mixture is further heated to 100° C. with stirring. After a total of 1 hour at 100° C., the composition is allowed to cool to 45° C. and 736 g water is added in one portion. At 45° C., 40 g of 50% aqueous sodium hydroxide solution is added dropwise over 20 minutes and the reaction mixture is maintained below 50° C. After maintaining the composition at temperature for 1 hour, it is poured into jars without filtration. The product composition is an orange liquid.

Example 7

The critical micelle concentration ("CMC") of Surfactant A in water at 22° C. is determined by preparing solutions of the surfactant at differing concentrations. The presence of micelles is determined by the use of pinacyanol dye. The dye turns blue to indicate the presence of micelles. The results indicate that micelles are present at a surfactant concentration of 0.020±0.001 weight percent and above, which corresponds to the CMC. (These values and those in the following examples are corrected to reflect the actual amount of surfactant chemical present, exclusive of diluent water.)

Example 8

The solubility of Surfactant A in the presence of calcium ion is determined at 22° C. Mixtures of Surfactant A are prepared using water containing 0.001M, 0.01M, and 0.2M CaCl$_2$. At all concentrations tested, up to 10 times the critical micelle concentration (that is, up to 0.20 weight percent), the surfactant dissolves to form a clear solution without formation of precipitate. Formation of precipitate is determined by the use of pinacyanol dye as in Example 7. Since micelles and precipitate cannot coexist thermodynamically for single surfactant systems, the presence of a blue color, indicating the existence of micelles, likewise indicates the absence of precipitate. The absence of precipitate at all the concentrations evaluated indicates excellent hardness tolerance of Surfactant A.

Example 9

The extent to which Surfactant A is adsorbed to soil is tested by contacting solutions of various concentrations (equal to 0.5, 1.0, 2.0, 5.0, and 10.0 times the critical micelle concentration) of the surfactant with Canadian River Alluvium. The samples are equilibrated with periodic shaking for 1 week. A sample of the supernatant liquid is separated by pipetting and is tested for the presence of micelles by the pinacyanol dye assay. Knowledge of the feed concentration of the surfactant and the CMC is used to estimate the maximum amount of adsorption that could have occurred in order for micelles to remain in the solution. The results are shown in the Table:

| Surfactant Concentration in Feed (x CMC) | Micelles Remaining After Adsorption |
| --- | --- |
| 0.5 | No |
| 1.0 | No |
| 2.0 | questionable |
| 5.0 | Yes |
| 10.0 | Yes |

Based on the above test, the maximum estimated adsorption of surfactant onto the soil is 1×CMC×0.020 g/L×6 mL solution tested/1.2 g soil, which corresponds to 0.0010 g per 1 g soil. This represents exceptionally low adsorption. The combination of good hardness tolerance and low adsorption indicates that Surfactant A is particularly useful for treatment of soils in the presence of ambient hard water.

Example 10

Samples of soil contaminated with crude oil are tested for remediation effectiveness by use of the present surfactant. The soil, a sandy soil, is obtained from a former oil field tank site where the water table is located approximately 1.2 m beneath the surface. (The ground water level fluctuates over time by at least 0.6 m, leading to free phase crude oil being accumulated throughout the soil.) Testing is effected by obtaining 3 g samples of contaminated soil and combining with 15 mL of surfactant solution in a 40 mL vial. The contents are agitated for 30 minutes and the resulting mixture is separated by centrifugation. The liquid portion is removed by decantation and the solids are lightly rinsed with deionized water. The amount total petroleum hydrocarbons (TPH) in the samples after treatment is determined by washing the treated soil with methylene chloride and measurement of the amount of TPH in the wash. The percent removal of TPH from each sample is determined by comparison of the results with those obtained by washing a corresponding reference sample of untreated contaminated soil with methylene chloride and performing the corresponding analysis of TPH in the wash. The results of testing are shown in the following table. In each case the amount of surfactant employed in the solution is 0.25 times its critical micelle concentration.

| Surfactant | % TPH Removal |
| --- | --- |
| Surfactant A | 86 |
| Reference B[a] | 82 |

-continued

| Surfactant | % TPH Removal |
|---|---|
| Reference C[a] | 73 |
| Reference D[a] | 69 |
| none (water) | 61 |

[a]: a commercial surfactant

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent which may be customarily present in the commercial material, unless otherwise indicated. It is to be understood that the upper and lower amount, range, and ratio limits set forth herein may be independently combined. As used herein, the expression "consisting essentially of" permits the inclusion of substances which do not materially affect the basic and novel characteristics of the composition under consideration.

What is claimed is:

1. A method for remediating soil which is contaminated by one or more organic chemicals, comprising:

(a) contacting the contaminated soil with an aqueous composition comprising a surfactant represented by the structure $$(R-X-)_n-W$$

where;

each R is independently a hydrocarbyl group containing at least 8 carbon atoms, n is at least 1, W is a group containing at least 6 carbon atoms and at least one ether linkage for every 6 carbon atoms thereof, and each X is selected from the group consisting of

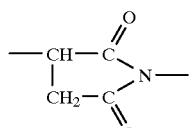

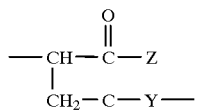

and

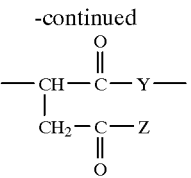

where:

each Y is independently —O— or —NR'—, each Z is independently OM or NR'$_2$, each R' is independently hydrogen or a $C_1$ to $C_{18}$ alkyl group, M is hydrogen, a monovalent metal or one valence of a polyvalent metal, a quaternary ammonium ion, a $C_1$ to $C_{18}$ alkyl group, or —(CH$_2$CHR"O)$_a$—H, where R" is hydrogen or a methyl group and a is 1 to 40;

wherein the group X is connected to the group W through the group Y or —NR'—;

whereby at least a portion of said hydrophobic organic chemicals become associated with said aqueous composition.

2. The method of claim 1 wherein the hydrophobic organic chemical comprises crude oil or a crude oil fraction.

3. The method of claim 1 wherein the hydrophobic organic chemical comprises a refined hydrocarbon.

4. The method of claim 1 wherein the hydrophobic organic chemical comprises a chlorinated hydrocarbon.

5. The method of claim 1 wherein each R is an alkyl group of about 12 to about 32 carbon atoms.

6. The method of claim 1 wherein each R is an alkyl group of about 16 to about 18 carbon atoms.

7. The method of claim 1 wherein each X is a group represented by the structure

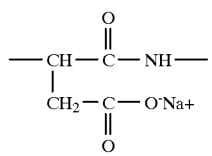

and positional isomers thereof.

8. The method of claim 1 wherein W is a divalent moiety containing about 20 to about 300 carbon atoms and comprising ethylene oxide monomers and propylene oxide monomers.

9. The method of claim 1 wherein W is represented by the structure

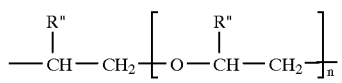

wherein n is at least 2 and each R" is independently hydrogen or methyl.

10. The method of claim 1 wherein W is represented by the structure

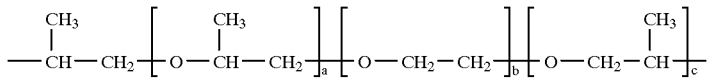

where a and c are integers which together equal 2 to about 20 and b is an integer in the range of 5 to about 70.

11. The method of claim 1 wherein the surfactant is represented by the structure

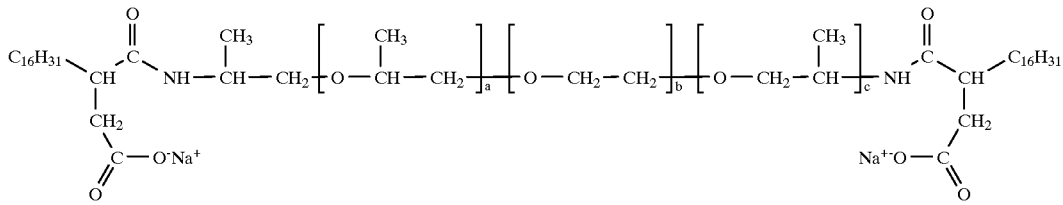

and positional isomers thereof, where a and c are integers which together equal 4 to 6, c is a positive integer, and b is an integer in the range of about 30 to about 50.

12. The method of claim 1 wherein n is 1 and W is a monovalent radical.

13. The method of claim 12 wherein W is represented by the structure

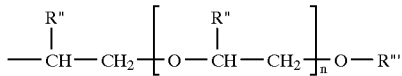

where each R" is independently hydrogen or methyl, R'" is hydrogen or a $C_1$ to $C_4$ alkyl group, and n is about 5 to about 42.

14. The method of claim 12 wherein W is represented by the structure

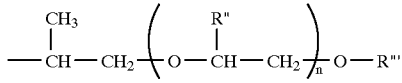

where each R" is independently hydrogen or methyl, the ratio of such hydrogen to methyl groups being about 3:1 to about 8:1, R'" is hydrogen or a $C_1$ to $C_4$ alkyl group, and n is about 5 to about 42.

15. The method of claim 13 wherein the ratio of hydrogen to methyl groups is about 3:1 to about 8:1 and n is about 5 to about 42.

16. The method of claim 1 wherein the surfactant is the reaction product of a hydrocarbyl-substituted succinic anhydride or a reactive equivalent thereof with at least one water-dispersible amine-terminated poly(oxyalkylene).

17. The method of claim 1 wherein the concentration of the surfactant in the aqueous composition is about 0.005 to about 5 weight percent.

18. The method of claim 17 wherein the concentration of surfactant is about 1 to about 3 weight percent.

19. The method of claim 17 wherein the concentration of surfactant is about 0.01 to about 0.5 weight percent.

20. The method of claim 1 wherein one or more additional surfactants are employed along with the surfactant $(R\text{—}X\text{—})_n\text{—}W$.

21. The method of claim 1 further comprising (b) removing said aqueous composition and organic chemicals associated therewith from the soil.

22. The method of claim 21 wherein the aqueous composition is injected into an area of contaminated soil and removed at a different location, whereby the aqueous composition passes through the contaminated soil and at least a portion of said hydrophobic organic chemicals become associated with said aqueous composition and are thereby removed from the soil.

23. The method of claim 1 wherein contaminated soil is removed from the ground and treated with an aqueous solution of the surfactant.

24. The method of claim 1 further comprising (b) subjecting the soil thus treated to the action of a biological process, whereby decontamination is effected.

25. The method of claim 23 wherein decontamination is effected in situ.

26. The method of claim 24 wherein the biological process is effected by naturally present bacteria.

27. The method of claim 24 wherein the biological process is effected by bacteria selected for the purpose of decontamination.

* * * * *